United States Patent [19]

Booker et al.

[11] Patent Number: 5,601,235

[45] Date of Patent: Feb. 11, 1997

[54] AEROSOL GENERATOR

[75] Inventors: David R. Booker, Weymouth; Kevin D. Horton, Poole, both of United Kingdom

[73] Assignee: United Kingdom Atomic Energy Authority, Harwell, United Kingdom

[21] Appl. No.: 340,869

[22] Filed: Nov. 15, 1994

[30] Foreign Application Priority Data

Dec. 4, 1993 [GB] United Kingdom .................. 9324938

[51] Int. Cl.$^6$ ............................ B05B 12/04; B05B 17/06
[52] U.S. Cl. ................... 239/4; 239/10; 239/63; 239/102.2
[58] Field of Search ................ 239/3, 4, 10, 102.2, 239/113, 112, 71, 74, 63

[56] References Cited

U.S. PATENT DOCUMENTS

| | | |
|---|---|---|
| 3,952,207 | 4/1976 | Leschonski . |
| 3,990,797 | 11/1976 | Neukermans . |
| 4,193,356 | 3/1980 | Vehe et al. ............................ 239/74 X |
| 4,361,400 | 11/1982 | Gray et al. ....................... 239/102.2 X |
| 5,229,171 | 7/1993 | Donovan et al. ................. 239/102.2 X |
| 5,358,182 | 10/1994 | Cappeau et al. ..................... 239/112 X |

FOREIGN PATENT DOCUMENTS

| | | | |
|---|---|---|---|
| 2290959 | 11/1990 | Japan ....................................... 239/71 |
| 1599117 | 10/1990 | U.S.S.R. ................................... 239/71 |

*Primary Examiner*—Kevin Weldon
*Attorney, Agent, or Firm*—William R. Hinds

[57] ABSTRACT

An aerosol generator (10) includes a plate (18) defining an orifice (20) through which a jet of liquid is projected, which breaks up into droplets. The plate (18) is vibrated to control the droplet size, and the size distribution. The droplet size distribution is monitored, and this information is used to control the vibration to ensure the droplets are monodisperse and of the correct size. This can be achieved as follows: the droplets are diverted by a transverse air stream, and an optical image is obtained of the diverted jet (28) onto a linear array of photodetectors (34). The signals from the photodetectors represent the particle size distribution, and are supplied as input to a computer (36) whose output is used to control the vibration of the plate (18).

8 Claims, 1 Drawing Sheet

AEROSOL GENERATOR

This invention relates to an aerosol generator, particularly but not exclusively to a generator of substantially monodisperse aerosol particles, and to a method of making an aerosol using such a generator.

Monodisperse aerosols of known particle size are used for a variety of purposes including the calibration of particle sizing instruments, and the testing of particle trapping equipment. The term particle in this context should be taken to encompass both solid particles and liquid droplets. A generator suitable for making substantially monodisperse test particles is the vibrating orifice aerosol generator, in which a jet of liquid is formed by passing liquid through an orifice in a plate and the plate is vibrated. Even without the vibration, the jet, initially a column of liquid, would be unstable as any variations in diameter cause it to break up to form a jet of droplets; with a vibrating plate a jet of droplets is formed almost instantaneously, and if the amplitude and frequency of the vibration have appropriate values, the droplets are monodisperse. The size of the droplets is approximately twice the diameter of the orifice, and can in a particular case be calculated from the flow rate of the liquid and the frequency. If the droplets consist of dispersion (a solution or suspension) of material in a volatile liquid then the droplets will dry to give particles of the dispersed material of uniform mass, whose size also depends on the concentration of the dispersion. One such aerosol generator is described by L. Strom in Rev. Sci. Inst., Vol. 40, No. 6 (June 1969) page 778. Such a generator can be set up to provide monodisperse particles, but in practice it is often found to go out of tune after a period of operation of up to a few hours, and to start producing particles of two or more sizes.

According to the present invention there is provided an aerosol generator comprising means to define an orifice, means to supply a liquid to one side of the orifice-defining means so a jet of liquid emerges from the orifice, and means to vibrate the orifice-defining means, means to monitor the size distribution of droplets in the jet after it has emerged, and means responsive to signals from the monitoring means to control the means causing the vibration.

The generator thus incorporates feedback, so continuous, consistent production of monodisperse aerosol particles can be assured. The means causing the vibration is preferably piezoelectric vibrator, and the control may involve adjusting either the voltage or the frequency applied to it.

Preferably the monitoring means comprises a nozzle arranged to form a gas stream to divert the liquid jet after it has emerged, and an optical system to form an image of the diverted liquid jet on a linear array of photodetectors, the photodetectors providing the signals to the control means. The nozzle is preferably between 3 and 25 mm away from the orifice, most preferably between 3 and 5 mm and 10 mm, for example 5 mm, and the gas stream is preferably transverse to the initial direction of the jet. The gas stream is preferably sufficient to divert the jet through an angle of between 10° and 30°, for example about 20°. The array is in a plane approximately transverse to the mean direction of the diverted jet.

The control means may utilize a neural network to analyse and interpret the signals. Alternatively it might utilize computer analysis, or dedicated hardware. The gas stream diverts particles or droplets of different sizes through different angles, the smaller droplets being diverted the most. The use of such a gas stream is referred to in the article by L. Strom mentioned earlier. The gas stream also has the effect that the droplets are sufficiently dispersed that droplets do not coalesce into double or triple droplets. Such coalescence can be further suppressed by diverting the jet of droplets by a second gas stream after the size distribution has been monitored, and this second gas stream may be sufficient to divert the jet of droplets through a larger angle, for example in the range 40° to 70°, say 45°.

The preferred embodiment utilises an orifice of diameter in the range 2 to 30 microns. Clearly the liquid must be filtered before being supplied to the orifice, but nevertheless blockages may occur. Preferably the generator includes means to detect any blockage of the orifice, and if any blockage is detected to clean the orifice. This may be achieved by supplying clean liquid to the orifice, or by supplying clean liquid to the outside of the orifice and pumping liquid through the orifice in the reverse direction to normal. Once the orifice has been cleared the outer face of the orifice-defining means is preferably cleaned of any liquid, so a jet can more readily be formed. The blockage may be detected by monitoring the pressure of the liquid supplied to the orifice.

It may also be desirable to supply a pulse of air to the outer face of the orifice-defining means, during start-up of the generator, to remove any liquid which has collected there.

The liquid supplied to the orifice may be provided from two different supplies, with different concentrations of non-volatile material, so that by varying the proportions of the two liquids which are supplied the concentration in the liquid emerging in the droplets can be controlled. Hence the sizes of the solid particles formed after evaporation of the volatile liquid from the droplets can be controlled.

The invention will now be further described, by way of example only, and with reference to the accompanying drawings, in which.

Figure 1:
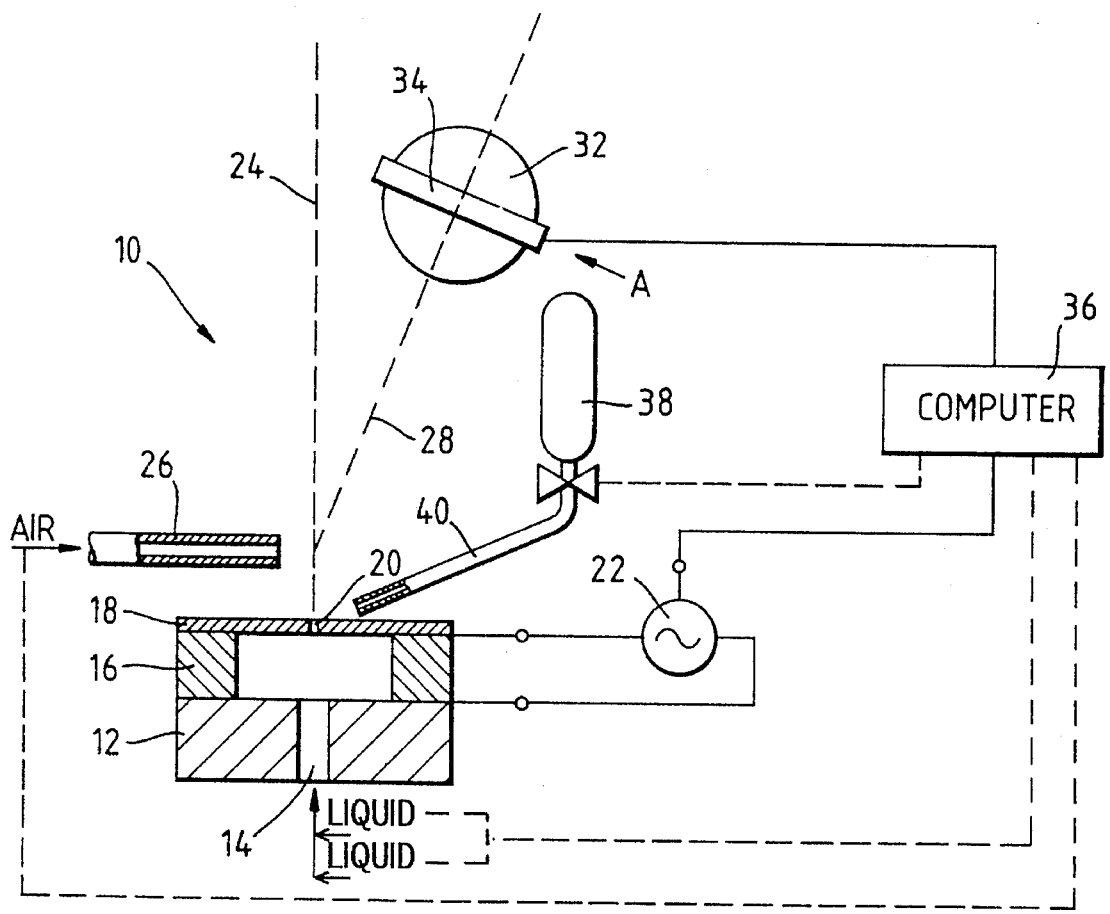
FIG. 1 shows a diagrammatic sectional view of an aerosol generator.

Referring to FIG. 1, an aerosol generator 10 includes a base plate 12 defining a duct 14 to which is supplied a liquid. Alternatively, as schematically shown, two liquids might be supplied simultaneously to the duct, the liquids differing in their concentrations of a non-volatile material so that by adjusting the proportions of the two liquids supplied to the duct 14 the concentration of the non-volatile material in the resulting liquid can be controlled. To the upper surface of the base plate 12 is fixed an annular piezoelectric transducer 16, to whose upper surface is fixed an orifice plate 18 defining a circular orifice 20 of diameter 20 microns. The transducer 16 is electrically connected to a computer-controlled power supply 22. In operation a jet of liquid therefore emerges along the trajectory shown by the broken line 24.

Figure 2:
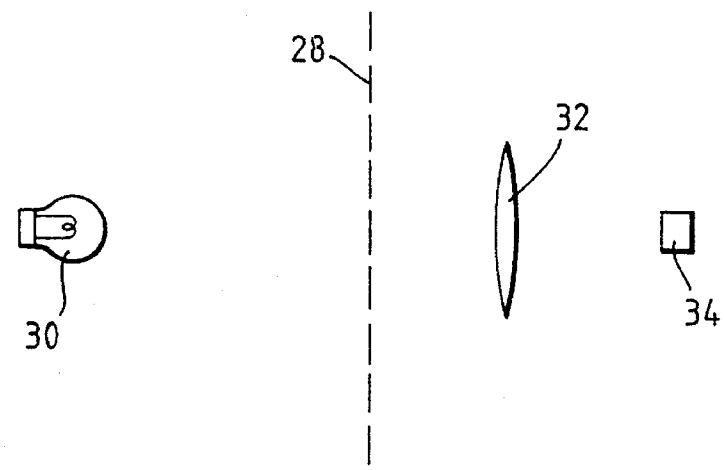
FIG. 2 shows a view in the direction of arrow A of FIG. 1.

About 5 mm above the orifice plate 18 is supported a tube 26 of diameter 1 mm connected to a source of air, so that a stream of air flows transverse to the trajectory 24. This diverts the jet of liquid through an angle of about 20° onto a trajectory such as that shown by the broken line 28. About 40 mm along the trajectory 28, the jet passes through an optical system shown also in FIG. 2: a light source 30 is arranged at one side of the trajectory 28, to illuminate the jet, and light scattered by droplets in the jet is focused by a lens 32 onto a linear array 34 of 1024 photodetectors; the array 34 as shown in FIG. 1 extends in a direction at right angles to the expected trajectory 28. Electrical signals from the photo-detectors in the array 34 are supplied to a computer 36, which analyses them to determine the nature of the jet, and provides control signals to the power supply 22 to ensure a desired mode of operation of the generator 10.

The computer 36 is also connected, as indicated by broken lines, to the means (not shown) supplying the liquid or liquids to the duct 14, and to the means (not shown) supplying the air to the tube 26, so as to provide control signals to them, for example to control the flow rate of the liquid or the flow rate of the liquids. In addition the computer 36 also provides control signals to means 38 for supplying a pulse of compressed air to a tubular nozzle 40 directed towards the orifice 20. If liquid collects on the upper surface of the orifice plate 18, a series of pulses of compressed air from the nozzle 40 will remove it If the liquid flow rate is large enough the liquid will emerge as a jet. For an orifice of diameter d, and a liquid of density $\rho$ and surface tension $\Gamma$, the minimum velocity v for a jet to form is:

$$v = \sqrt{\frac{8\gamma}{\rho d}}$$

(see Lindblad et al., J. Sci. Inst., Vol. 42, page 635 (1965)), although if a layer of liquid has collected on the upper surface of the orifice plate 18, a higher velocity will be required. Such a jet of liquid is unstable, as any variations in jet diameter will grow exponentially and break up the jet into droplets, for variations which are at least a distance $\pi d$ apart along the jet. The diameter of droplets formed spontaneously (i.e. with no power supply 22) is typically about twice the diameter of the orifice 20. Vibration of the orifice plate 18 (at a frequency f) imposes cyclical variations on the jet diameter at a separation L along the jet given by:

$$L = vf$$

Theoretically the optimum separation L, for which the disturbances will grow the most rapidly, is given by:

$$L = \sqrt{2}\ \pi d = 4.44\ d$$

but in practice uniform droplets can be produced for a range of different values of L from about 3.5 d up to about 7 d (depending to some extent on the amplitude of the vibration of the plate 18). For a fixed liquid flow rate Q, and so a fixed jet velocity v, there is consequently a range of different frequencies f at which uniform, monodisperse droplets can be expected to be formed. As long as the droplets are monodisperse the size of each droplet can readily be calculated, its diameter D being given by:

$$D = \sqrt[3]{\frac{6Q}{\pi f}}$$

If each droplet contains a non-volatile material in a volatile liquid, then after the liquid has evaporated there will be monodisperse particles of the non-volatile material.

In operation the jet breaks up into droplets almost instantaneously, certainly within 1 mm of the orifice 20. In practice it has been found that in prolonged operation, for example over a period of hours, the generator 10 starts to produce a mixture of different droplet sizes. The smaller droplets are diverted more by the air stream, so that the diverted jet no longer follows the trajectory 28 but rather a range of different trajectories either size of the trajectory 28 of FIG. 1, depending on what particle sizes are present. The signals produced by the array 34 of photodetectors correspond to the numbers of droplets passing different positions along a line perpendicular to the trajectory 28 (parallel to the array 34) and so represent the numbers of droplets of different sizes, i.e. the droplet size distribution. The computer 36 can hence determine if the droplets are monodisperse, and hence supplies control signals to the power supply 22 to adjust either its voltage or its frequency to maintain a monodisperse stream of droplets.

Typically, with the orifice 20 which is of diameter 20 microns, liquid might be supplied at a rate in the range 0.1 to 0.5 ml/min, while the transducer 16 might vibrate at a frequency in the range 45–65 kHz. If the drive frequency is altered to maintain a monodisperse stream, a change of a few tens of hertz is usually sufficient, so the resulting particle diameter is not significantly changed.

It will be appreciated that the generator 10 might differ in various ways from that described above. For example the means causing vibration of the plate 18 might be such as to cause bowing of the plate instead of linear motion of the plate. The orifice might be of a different size, so as to produce droplets of a different size, and the requisite frequency range of the generator 22 would consequently have to be different. The array 34 might include a different number of photodetectors, for example 512 or 2048. The tube 26 supplying the diverting air stream might have a different diameter, for example in the range 0.5 to 2.0 mm. And there might be a further tube (not shown) to divert the jet of particles a second time, for example through 45°, after they have passed beyond the optical monitoring system 30, 32, 34, so as to separate the droplets further from their neighbours and so suppress the coalescence of adjacent droplets. This second diversion may take place in the same plane as that caused by the air from the tube 26 (i.e. the plane of FIG. 1) so that the droplets emerge in a direction almost at right angles to their initial trajectory 24.

We claim:

1. An aerosol generator comprising means to define an orifice, means to supply a liquid to one side of the orifice-defining means so a jet of liquid emerges from the orifice, and means to vibrate the orifice-defining means, means to monitor the size distribution of droplets in the jet after it has emerged, and means responsive to signals from the monitoring means to control the means causing the vibration.

2. An aerosol generator as claimed in claim 1 wherein the means to cause the vibration is a piezoelectric vibrator, and the control means adjusts either the voltage or the frequency applied to it.

3. An aerosol generator as claimed in claim 1 wherein the monitoring means comprises a nozzle arranged to form a gas stream to divert the liquid jet after it has emerged, and an optical system to form an image of the diverted liquid jet on a linear array of photodetectors, the photodetectors providing the signals to the control means.

4. A method of generating an aerosol comprising supplying a liquid to one side of an orifice-defining means so a jet of the liquid emerges from the orifice, vibrating the orifice-defining means, monitoring the size distribution of droplets in the jet after it has emerged, and in response to signals from the monitoring means controlling the means causing the vibration.

5. A method as claimed in claim 4 wherein the size distribution is monitored by diverting the liquid jet after it has emerged, by means of a gas stream, and forming an optical image of the diverted liquid jet on a linear array of photodetectors.

6. A method as claimed in claim 4 wherein the liquid supplied to the orifice is provided from two sources differing in their concentrations of a non-volatile material, the proportions of the liquids supplied from the two sources being adjusted to control the concentration of the non-volatile material in the liquid emerging in the droplets.

7. A method as claimed in claim 4 also comprising supplying a pulse of air to the outer face of the orifice-defining means, prior to creation of the liquid jet, to remove any liquid which has collected there.

8. An aerosol generator comprising a plate defining an orifice of diameter in the range 2 to 30 microns, means to supply liquid to one side of the plate at such a pressure that a jet of the liquid emerges from the orifice, a piezoelectric vibrator arranged to vibrate the plate, the vibrator being connected to an electric power supply, nozzle means to create a gas stream generally transverse to the jet, which gas stream would hit the jet of droplets at a location in the range 3 mm to 25 mm from the orifice plate and divert the jet of droplets, an optical system to form an image of the diverted jet of droplets on a linear array of photodetectors, and control means responsive to electrical signals from the photodetectors to adjust the electrical power supply to the vibrator.

* * * * *